United States Patent [19]

Christensen et al.

[11] Patent Number: 4,871,367

[45] Date of Patent: Oct. 3, 1989

[54] SURGICALLY IMPLANTED PROSTHESIS

[75] Inventors: James M. Christensen, Los Angeles County; David A. Westerfield, San Diego County, both of Calif.

[73] Assignee: Sutter Biomedical Corporation, San Diego, Calif.

[21] Appl. No.: 92,415

[22] Filed: Sep. 3, 1987

[51] Int. Cl.$^4$ .............................................. A61F 2/42
[52] U.S. Cl. .................................................... 623/21
[58] Field of Search .............................. 623/21, 18, 20

[56] References Cited

U.S. PATENT DOCUMENTS

| | | | |
|---|---|---|---|
| 3,593,342 | 7/1971 | Niebauer | 623/21 |
| 3,875,594 | 4/1975 | Swanson | 623/4 |
| 4,059,854 | 11/1977 | Laure | 623/21 |
| 4,193,139 | 3/1980 | Walker | 623/21 |
| 4,229,839 | 10/1980 | Schwemmer | 623/21 |

*Primary Examiner*—Richard J. Apley
*Assistant Examiner*—David J. Isabella
*Attorney, Agent, or Firm*—Flehr, Hohbach, Test, Albritton & Herbert

[57] ABSTRACT

A surgically implantable prosthesis for replacing a bone joint, specifically the knuckle, of an individual is disclosed herein. The prosthesis includes a one-piece main body of flexible, inert material including first and second spaced apart end sections and a narrower web extending between and joining the sections together for flexing movement about a particular flexing axis through the web, whereby the main body functions as a hinge. First and second elongated stems connected to and extend out from these end sections in directions normal to the flexing axis and away from one another. In accordance with one feature of the prosthesis disclosed herein, a specific one of the stems is laterally offset in a specific way with respect to the flexing axis. In accordance with another feature, the end sections and web of the main body together define the key-hole shaped groove across one side of the web between the end sections.

12 Claims, 1 Drawing Sheet

U.S. Patent    Oct. 3, 1989    4,871,367
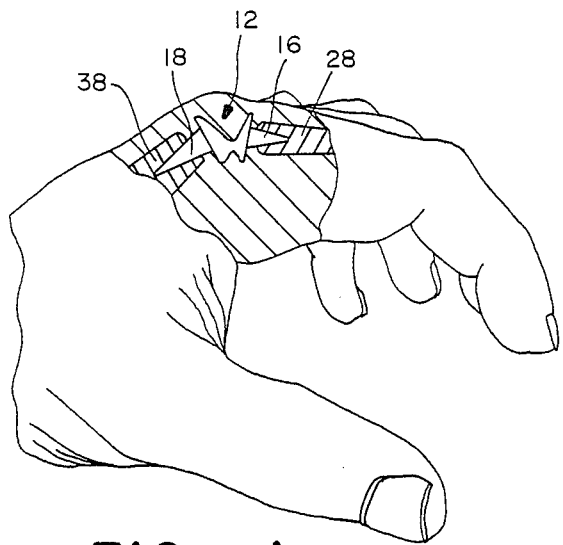
FIG.—1
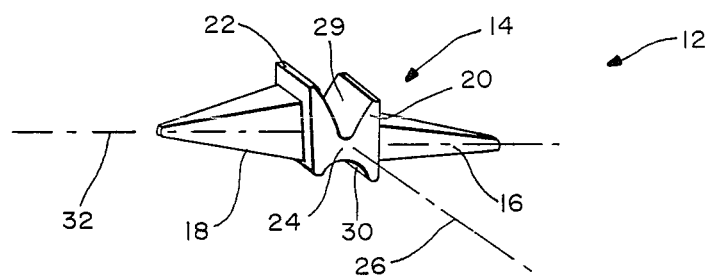
FIG.—2
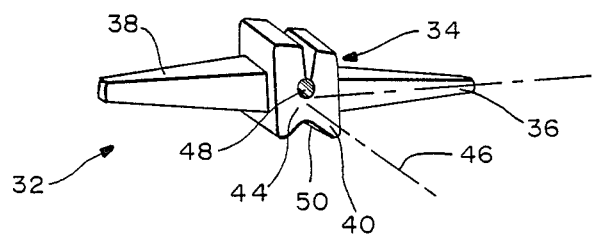
FIG.—3
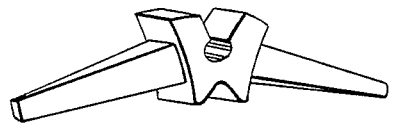
FIG.—4

SURGICALLY IMPLANTED PROSTHESIS

The present invention relates generally to surgically implantable prosthetic devices for replacing skeletal joints and more particularly to a prosthesis designed to flex in a specific way.

There are a number of different types of surgically implantable prosthetic devices, as exemplified by those disclosed in Swanson U.S. Pat. Nos. 3,462,765 and 3,875,594 and the Niebauer et al. U.S. Pat. No. 3,593,342. This latter patent discloses a one-piece prosthesis constructed of flexible inert material and consists of a main body which serves as a hinge and opposing stems which serve to implant the prosthesis in place. As illustrated in the Niebauer et al. patent, its main body is comprised of a pair of spaced apart end sections and a narrower web extending between and joining the end sections together for flexing movement about a particular flexing axis through the web.

In the Niebauer et al. prosthetic device, the end sections and web of its main body together define opposing generally V-shaped grooves across opposite sides of the web between the end sections and the stems are positioned in the same plane as the flexing axis of the main body. As will be seen hereinafter, applicants have found that both of these design aspects of a prosthetic device of the general type disclosed by Niebauer et al. can be modified to provide a substantially improved implant.

In view of the foregoing, it is one object of the present invention to provide a surgically implantable prosthesis having a main hinge body and a pair of opposing stems which are positioned relative to one another so as to accurately duplicate the natural bending action of the joint being replaced by the prosthesis.

Another object of the present invention is to provide a surgically implantable prosthesis having a main hinge body which is designed to display along flexing life.

As will be seen hereinafter, the surgically implantable prosthesis disclosed herein, like previous prosthetic devices consists of, a one-piece main body of flexible inert material and first and second elongated stems. The one-piece main body includes first and second spaced apart end sections and a narrower web extending between and joining the end sections together for flexing movement about a particular flexing axis through the web, whereby the main body functions as a hinge. The elongated stems are connected to and extend out from the end sections of the main body in directions normal to the flexing axis and away from one another.

In accordance with one feature of the present invention, a specific one of the stems forming part of the surgically implantable prosthesis disclosed herein is positioned with respect to the main body of the prosthesis such that its axis of elongation is laterally offset to a specific side of the flexing axis of its web. In an actual working embodiment, the other stem is positioned in alignment with the flexing axis, that is, in the same plane and both stems are implantable within cooperating intramedullary canals of adjacent bones defining the bone joint being replaced by the prosthesis. In this actual embodiment, the particular bone joint being replaced is an individuals knuckle joint. Moreover, in this embodiment, the laterally offset stem is implanted within the intramedullary canal of the joints' metacarpal bone so that the flexing axis is on the palmar or volar side of the offset stem while the aligned stem is implanted into the canal of the adjacent proximal phalanx. As will be discussed hereinafter, this positional relationship allows the overall prosthesis to flex in a way which more accurately duplicates the natural flexing action of an individual's knuckle.

In accordance with another feature of the prosthesis disclosed herein, the end sections and web of its main body together define a key-hole shaped groove across one side of the web between the end sections. In an actual working embodiment, the end sections of the web together define a generally V-shaped groove across the opposite side of the web between its end sections. As will be seen hereinafter, this particular design enhances the flexing life of the overall prosthesis.

The present invention will be described in more detail hereinafter in conjunction with the drawings wherein:

FIG. 1 is a side elevational view, partial end section, of a human hand, specifically illustrating a surgically implanted prosthesis which is designed in accordance with one embodiment of the present invention and which is shown in place of a knuckle joint of the hand;

FIG. 2 is an enlarged perspective view of the prosthesis illustrated in FIG. 1;

FIG. 3 is an enlarged perspective view of a surgically implantable prosthesis designed in accordance with a second embodiment of the present invention and shown in a relaxed state; and FIG. 4 is a side elevational view of the prosthesis of FIG. 3 shown in a flexed positioned.

Turning now to the drawings, wherein like components are designated by like reference numerals throughout the figures, attention is first directed to FIG. 1 which illustrates a human hand 10 partially broken away to illustrate the knuckle joint of one finger. As seen there, the knuckle joint has been replaced with a prosthesis 12 designed in accordance with the present invention. Referring to FIG. 2 in conjunction with FIG. 1, the prosthesis is shown including a one-piece main body 14 constructed of flexible inert material, for example, medical grade silicone, and a pair of elongated stems 16 and 18 preferably constructed of the same material as the main body and integrally formed with main body 14 as a single unit.

Still referring to FIGS. 1 and 2, main body 14 is shown including first and second spaced apart end sections 20 and 22 and a narrower web 24 extending between and joining the end sections together for flexing movement about a flexing axis generally indicated at 26, whereby the main body functions as a hinge. The two stems 16 and 18 are connected to the main body 14, preferably integrally so, as indicated above, and extend out from end sections 20 and 22, respectively, in directions normal to flexing axis 26 and away from one another. As seen specifically in FIG. 1, stem 16 is implanted within a cooperating intramedullary canal of an adjacent proximal phalanx bone 28 on one side of the knuckle joint being replaced while stem 18 is implanted within a cooperating intramedullary canal of the adjacent metacarpal bone 30 on the other side of the joint.

As best seen in FIG. 2, the end sections 20 and 22 of main body 14 are wider and thicker than the width and thickness of stems 16 and 18 in the area where the stems are connected to the end sections. As used herein, the width of main body 14 and stems 16 and 18 is measured vertically in FIG. 2 while the thickness of each is measured along axis 26, that is, into the plane of the paper as viewed in FIG. 1. With this nomenclature in mind, it can also be seen that web 24 is equal in thickness to end sections 20 and 22 but substantially narrower than the stem connecting ends of these end sections. The end sections and the web together define opposing generally V-shaped grooves 29 and 31 across opposite sides of the web between the end sections.

To the extent thus far described, overall prosthesis 12 is similar in design to, for example, the prosthetic device illustrated in the Niebauer et al. U.S. Pat. No. 3,593,342. However, as indicated above, the stems of that device are both aligned and in the same plane as the flexing axis of its body. In accordance with the present invention, while this may be the case with respect to the elongation axis of stem 16, the elongation of stem 18 is disposed laterally to one side of the plane containing flexing axis 26. As viewed in FIG. 1, the elongation axis of stem 18, generally indicated at 32 in FIG. 2 is disposed in a plane above flexing axis 26 such that the latter lies on the palmar or volar side of the offset stem and not in the same plane as the stem. This positional relationship is critical if the overall prosthesis is to flex in a way which accurately duplicates the flexing movement of the human knuckle joint, as stated previously.

Turning now to FIGS. 3 and 4, attention is directed to a surgically implantable prosthesis 32 designed in accordance with a second embodiment of the present invention. Like prosthesis 12, prosthesis 32 includes a one-piece main body 34 of flexible inert material, for example medical grade silicone, and a pair of elongated stems 36 and 38, preferably constructed of the same material as body 34 and preferably integrally formed with the latter as a single unit. Main body 34 includes a pair of spaced apart end sections 40 and 42 and a narrower web 44 extending between and joining end sections 40 and 42 together for flexing movement about flexing axis 46, whereby the main body functions as a hinge. The elongated stems 36 and 38 connect to and extend out from end sections 40 and 42, respectively, in directions normal to flexing axis 46 and away from one another.

Like prosthesis 12, in an actual working embodiment, the end sections of main body 34 are wider and thicker than the width and thickness of stems 36 and 38 in the area where the stems are connected to the end sections. In the same embodiment, the web is equal in thickness to the end sections and the elongation axis of stem 38 is laterally offset with respect to flexing axis 46 such that the flexing axis is on the palmar or volar side of the stem in the same manner as stem 18 and for the same reasons. Stem 36, like previously described stem 16, may be disposed in the same plane as axis 46 and, in the actual working embodiment, it is so positioned.

As best illustrated in FIG. 3, with prosthesis 32 in its relaxed state, its end sections 40 and 42 and web 44 together define a key-hole shaped groove 48 across one side of web 44 between end sections 40 and 42. The end sections and web together define a generally V-shaped groove 50 on the opposite side of the web. The advantage of this groove configuration may be better understood by referring back to the V-shaped groove configurations of prosthesis 12. When that prosthesis flexes about its web 24, the resultant stresses in the material are concentrated along the flexing axis 26. However, when prosthesis 32 is flexed, note that the cylindrical part of the key-hole groove forms the shape of an oval, as illustrated in FIG. 4. As a result, the entire surface defining the cylinder/oval part of the groove takes up the stresses resulting from the flexing action, spreading these stresses out over a much larger area and thereby increasing the flexing life of the overall prosthesis as compared to, for example, prosthesis 12.

Both features of the present invention, that is, the use of the laterally offset stem and a key-hole shaped groove, have been incorporated into a prosthesis especially designed to replace a human knuckle joint. However, it is to be understood that the features could be incorporated into other joints. Moreover, while it is critical to the first of these two features of the present invention to have a specific one of the stems laterally offset with respect to the flexing axis of the prosthesis, the other stem may or may not be laterally offset, as this is not critical.

What is claimed is:

1. A surgically implantable prosthesis for replacing a knuckle joint, comprising:
   (a) a one-piece main body of flexible inert material including first and seoncd spaced-apart end sections and a narrower web extending between and joining said end sections together for flexing movement about a particular flexing axis through the web, whereby the main body functions as a hinge, said end sections and said web together defining a key-hole shaped groove across one side said web between said end sections, said groove including a lowermost through-hole segment having a circular cross-section defining the top of the web and a generally v-shaped segment extending up from and opening into said through-hole between said end sections; and
   (b) first and second stems connected to and extending out from the first and second end sections of said main body in directions normal to said flexing axis and away from one another, said first and second stems being implantable within cooperating intramedullary canals of adjacent metacarpal and proximal phalanx bones, respectively, defining said knuckle joint.

2. A prosthesis according to claim 1 wherein said end sections and web of said main body together define a generally V-shaped groove across the side of said web opposite said key-hole shaped groove and between said end sections.

3. A prosthesis according to claim 1 wherein; said first stem being positioned with respect to said main body such that the flexing axis of said web is laterally offset to the palmar side of the elongation axis of said first stem.

4. A prosthesis according to claim 1 wherein said end sections of said main body are wider and thicker than the width and thickness of said stems in the area where the stems are connected to said end sections.

5. A prosthesis according to claim 4 wherein said web is equal in thickness to said end sections of said main body.

6. A prosthesis according to claim 5 wherein said end sections and web of said main body together define a generally V-shaped groove across the side of said web opposite said key-hole shaped groove and between said end sections.

7. A prosthesis according to claim 1 wherein said second stem is positioned with respect to said main body such that its axis of elongation is in the same plane as said flexing axis.

8. A one-piece surgically implantable prosthesis of flexible inert material for replacing a bone joint formed by adjacent first and second bones, the latter of which is intended to move back and forth in a vertical plane primarily below a second horizontal plane through said first bone, comprising:
  (a) a main body including first and second spaced-apart end sections and a narrower web extending between and joining said end sections together for flexing movement about a particular flexing axis through the web, whereby the main body functions as a hinge, said end sections and said web together defining a key-hole shaped groove across one side of the web between said end sections, said groove including a lowermost through-hole segment having a circular cross-section defining the top of the web and a generally V-shaped segment extending up from and opening into said through-hole defining said end section; and
  (b) first and second elongated stems connected to and extending out from the first and second end sections of said main body in directions normal to said flexing axis and away from one another, and implantable within cooperating intramedullary canals of said adjacent first and second bones respectively, defining said bone joint, said first stem being positioned with respect to said main body such that its axis of elongation is laterally offset to above the flexing axis of said web in a way which located said flexing axis below said horizontal plane.

9. A prosthesis according to claim 8 wherein said end sections of main body are wider and thicker than the width and thickness of said stems in the area where the stems are connected to said end sections.

10. A prosthesis according to claim 9 wherein said web is equal in thickness to said end sections of said main body.

11. A prosthesis according to claim 8 wherein said end sections and web of said main body together define a generally V-shaped groove across the side of said web opposite said key-hole shaped groove and between said end sections.

12. A prosthesis according to claim 11 wherein said web is equal in thickness to said end sections of said main body.

* * * * *